United States Patent [19]

Samreth et al.

[11] Patent Number: 4,996,347
[45] Date of Patent: Feb. 26, 1991

[54] NOVEL BETA-D-PHENYLTHIOXYLOSIDES, THEIR METHOD OF PREPARATION AND THEIR USE AS THERAPEUTICS

[75] Inventors: Soth Samreth, Longvic; François Bellamy, Saulon La Chapelle; Jean Millet, Saulon La Rue, all of France

[73] Assignee: Fournier Innovation et Synergie, Paris, France

[21] Appl. No.: 371,775

[22] Filed: Jun. 27, 1989

Related U.S. Application Data

[62] Division of Ser. No. 185,422, Apr. 25, 1988, Pat. No. 4,877,808.

[30] Foreign Application Priority Data

May 4, 1987 [FR] France .................... 87 06237

[51] Int. Cl.$^5$ ............................. C07C 321/26
[52] U.S. Cl. .................... 558/411; 558/415; 558/423; 568/62; 568/63; 568/65; 568/67
[58] Field of Search ............ 558/411, 415, 423; 568/62, 63, 65, 67

[56] References Cited

U.S. PATENT DOCUMENTS 3,949,002 4/1976 Feasey et al. .................. 568/63
4,134,993 1/1979 Evans et al. .................. 568/63

FOREIGN PATENT DOCUMENTS 0302321 2/1989 European Pat. Off. ............ 568/63

OTHER PUBLICATIONS

Chemical Abstracts, vol. 62, Abst. No. 524a.
Chemical Abstracts, vol. 64, Abst. No. 17549d.
Chemical Abstracts, vol. 77, Abst. No. 48036h.

Primary Examiner—Joseph Paul Brust
Assistant Examiner—Jacqueline Haley
Attorney, Agent, or Firm—Fleit, Jacobson, Cohn, Price, Holman & Stern

[57] ABSTRACT

The present invention relates, by way of novel industrial products, to osides selected from the group consisting of:

(i) the β-D-phenylthioxylosides of the formula:

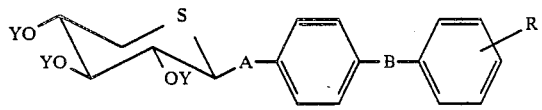

in which:

R represents a hydrogen atom, a halogen atom, a nitro group or a cyano group,
A represents the sulfur atom or the oxygen atom,
B represents a $CH_2$, CHOH or CO group and
Y represents the hydrogen atom or an acyl group; and
(ii) epimers thereof when B is CHOH.

These products are useful in therapy as antithrombotics.

1 Claim, No Drawings

NOVEL BETA-D-PHENYLTHIOXYLOSIDES, THEIR METHOD OF PREPARATION AND THEIR USE AS THERAPEUTICS

This is a division of application Ser. No. 185,422 filed Apr. 25, 1988 now U.S. Pat. No. 4,877,808.

The present invention relates, by way of novel industrial products, to the β-D-phenylthioxyloside derivatives of the formula I below. It also relates to their method of preparation and their application in therapy as antithrombotics, especially venous antithrombotics.

European Patent Document B-0051023 has already proposed benzoylphenyloside and α-hydroxybenzylphenyloside derivatives as antiulcer agents, platelet aggregation inhibitors, antithrombotics and cerebral oxygenators.

European Patent Document A-0133103 also discloses benzylphenylosides which are useful as hypocholesterolemics and hypolipidemics, some of these compounds, in particular the product of Example 1, having antithrombotic effects as well.

It has now been found that the β-D-phenylthioxyloside derivatives according to the invention, which are structurally different from the known products of the prior art, are useful in the treatment and prevention of diseases associated with circulatory disorders, especially as venous antithrombotics.

Unexpectedly, the derivatives according to the invention have antithrombotic properties which are greatly superior to those of the known products of the prior art, cf. the results of the comparative tests collated in Table III below.

The novel products according to the invention are selected from the group consisting of:

(i) the β-D-phenylthioxylosides of the formula:

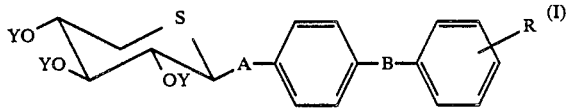

in which:

R represents a hydrogen atom, a halogen atom, a nitro group or a cyano group,

A represents the sulfur atom or the oxygen atom,

B represents a $CH_2$, CHOH or CO group and

Y represents the hydrogen atom or an acyl group; and (ii) epimers thereof when B is CHOH.

The hydroxyl groups of the β-D-thioxylose residue are capable of being acylated, especially acetylated. The present invention therefore includes the derivatives of the formula I in which the hydroxyl groups of the β-D-thioxylose residue are acylated, especially acetylated.

The fluorine, chlorine and bromine atoms may be mentioned among the halogen atoms included in the definition of the group R, the preferred halogen atom being the chlorine atom.

Among the acyl groups which are suitable according to the invention, there may be mentioned those which contain a total of 2 to 5 carbon atoms, the preferred acyl group being $CH_3CO$.

The compounds of the formula I and the corresponding acylated compounds can be prepared according to a glycosidation reaction wherein:

(i) a compound of the formula:

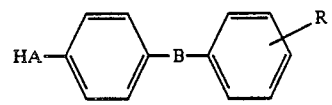

in which A, B and R are defined as above, is reacted with a thioxylose derivative selected from the group consisting of the halogenoacylthioxylosides and acylthioxylosides of the formulae:

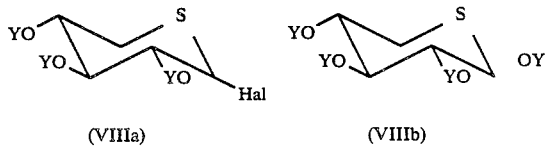

in which Hal represents a halogen atom, such as Cl or Br (the bromine atom being the preferred halogen atom here), and Y represents an acyl group, especially an aliphatic acyl group containing a total of 2 to 5 carbon atoms and preferably the acetyl group, in an inert solvent, at a rate of 1 mol of II to about 1.1 to 1.2 mol of thioxylose derivative, in the presence of an acid acceptor or a Lewis acid, and (ii) if necessary, a deacylation reaction is carried out at a temperature between room temperature (15°-25° C.) and the reflux temperature of the reaction medium, in a $C_1$-$C_4$ lower alcohol (preferably methanol), in the presence of a metal alcoholate (preferably magnesium methylate or sodium methylate).

In this method, it is important in stage (i) that the compound VIIIa is in the α configuration. On the other hand, the compound VIIIb can be in the α or β configuration or a mixture of both configurations.

The acylated or non-acylated compounds of the formula I in which B represents either CHOH or $CH_2$ can also be obtained by reduction, according to a method known per se, of the compounds of the formula I (acylated or non-acylated) in which B represents CO or CHOH.

Again, the acylated or non-acylated compounds of the formula I in which B represents CO can be obtained by oxidation, according to a method known per se, of the compounds of the formula I (acylated or non-acylated) in which B represents $CH_2$ or CHOH.

The following are recommended among the glycosidation methods known to those skilled in the art:

the KOENIGS-KNORR method (described in "The Carbohydrates, Chemistry and Biochemistry", 2nd Edition, New York and London: Academic Press (1972), volume IA, pages 295–301), which involves condensing a phenol or a thiophenol of the formula II with a halogenoacylthioxyloside VIIIa, in an inert solvent selected from polar and apolar solvents (for example dimethylformamide, tetrahydrofuran, dioxane, acetonitrile, nitromethane, benzene, toluene, xylenes and mixtures thereof), in the presence of a proton acceptor such as mercuric cyanide or silver triflate (silver trifluoromethylsulfonate); and the HELFERICH method (ibidem, pages 292–294), which involves condensing an acylthioxyloside VIIIb with a phenol or a thiophenol of the formula II, in an inert solvent selected from aromatic solvents, chlorinated solvents, ethers and mixtures thereof, in the presence of a Lewis acid.

In a preferred method of carrying out the invention, if A represents a sulfur atom in the compound of the formula II, it is recommended in stage (i) of the method to condense 1 mol of the thiol II with about 1.1 to 1.2 mol of halogenoacylthioxyloside VIIIa in an inert solvent selected from polar and apolar solvents, in the presence of mercuric cyanide.

It will be advantageous to use 2,3,4-tri-O-acetyl-1-bromo-α-D-5-thioxylopyranoside in a 1/1 (v:v) benzene/nitromethane mixture, in the presence of 1.1 to 1.3 mol of mercuric cyanide, at a temperature between 0° C. and the reflux temperature of the reaction medium, preferably at about 40°-50° C., for 1 to 4 hours, preferably for about 2 hours.

In another preferred method of carrying out the invention, if A represents an oxygen atom and B represents the methylene group in the compound of the formula II, it is recommended in stage (i) of the method to condense 1 mol of the phenol II with about 1.1 to 1.2 mol of halogenoacylthioxyloside VIIIa, in an inert solvent selected from aromatic solvents, chlorinated solvents, ethers and mixtures thereof, in the presence of silver triflate.

It will be advantageous to use 2,3,4-tri-O-acetyl-1-bromo-α-D-5-thioxylopyranoside in an anhydrous 1/1 (v:v) toluene/nitromethane mixture, in the presence of 1.1 to 1.3 mol of silver triflate, the reaction being carried out in the absence of light, at a temperature between 0° C. and 15° C., preferably at about 3° C., for 5 to 24 hours, preferably for about 12 hours.

In another preferred method of carrying out the invention, if A represents a sulfur atom in the compound of the formula II, it is also recommended in stage (i) of the method to condense 1 mol of the thiol II with about 1.1 to 1.3 mol of acylthioxyloside VIIIb, in an inert solvent selected from ethers, aromatic solvents, chlorinated solvents and mixtures thereof, in the presence of $SnCl_4$.

It will be advantageous to use 1,2,3,4-tetra-O-acetyl-α(or β)-D-5-thioxylopyranoside in methylene chloride, in the presence of 1.1 to 1.2 mol of $SnCl_4$, at a temperature between 0° C. and the reflux temperature of the reaction medium, preferably at about 20° C., for 1 to 5 hours, preferably for about 3 hours.

The glycosidation reaction leads in all cases to a mixture of the α and β isomers in variable proportions.

The β isomer is isolated by the methods known to those skilled in the art, for example by fractional crystallization or chromatography, especially flash chromatography, i.e. chromatography on a silica column under pressure according to the technique described by W. C. STILL et al. in J. Org. Chem. (1978), 42 (no. 14) 2923.

The reduction reactions which make it possible to obtain the acylated or non-acylated compounds of the formula I in which B is CHOH from the corresponding compounds in which B is CO use conventional reagents such as metal hydrides, like $LiAlH_4$, $KBH_4$ or $NaBH_4$, in inert solvents such as ether, tetrahydrofuran or lower alcohols, especially methanol and ethanol, at a temperature between 0° C. and room temperature (15°-25° C.), for 1 to 12 hours, the preferred metal hydride being $NaBH_4$ and the reaction preferably being carried out in methanol at a temperature of 20° C.

The reduction reactions which make it possible to obtain the acylated or non-acylated compounds of the formula I in which B is $CH_2$ from the corresponding compounds in which B is CO or CHOH use reducing agents such as metal hydrides, like $NaBH_4$ or $KBH_4$, preferably $NaBH_4$, in trifluoroacetic acid. The best method of carrying out the reaction in this case consists in introducing the reducing agent into a mixture containing the compound to be reduced and trifluoroacetic acid, at a temperature between the solidification temperature of the reaction medium and 0° C., preferably at 0° C., with an excess of reducing agent relative to the compound to be reduced, and, when the addition of the reducing agent is complete, in allowing the reaction to proceed for 0.5 to 12 hours, with stirring, at a temperature between 0° C. and 20° C. In practice, to solubilize the compound to be reduced, it is advantageous to use the trifluoroacetic acid in association with a chlorinated solvent, especially methylene chloride.

The oxidation reactions which make it possible to obtain the acylated or non-acylated compounds of the formula I in which B is CO from the corresponding compounds in which B is $CH_2$ use conventional oxidizing agents such as $CuSO_4/K_2S_2O_8$ or $Cr_2O_3$, in the presence of an organic base such as pyridine, in a polar or apolar solvent such as ethers, aromatic solvents, chlorinated solvents and mixtures thereof, preferably a 1/1 (v:v) water/acetonitrile mixture when using $CuSO_4/K_2S_2O_8$ and methylene chloride when using $Cr_2O_3$.

If appropriate, the derivatives obtained are subjected to deacylation, more particularly deacetylation, which is carried out at a temperature between room temperature and the reflux temperature of the reaction medium, in a $C_1-C_4$ lower alcohol, in the presence of the corresponding metal alcoholate. Preferably, methanol will be chosen as the lower alcohol and sodium or magnesium methanolate as the metal alcoholate.

The deacylation and reduction reactions (in particular conversion of CO to CHOH) can optionally be carried out in succession without isolating the intermediate compound formed.

The intermediate derivatives of the formula II in which A represents a sulfur atom are novel compounds except for the compounds in which B is CO when R is H or 4-Cl and B is $CH_2$ when R is H or 4-Cl.

To obtain these thiophenols, it is recommended to:

(i) condense, in a strong basic medium, dimethylaminothiocarbamoyl chloride of the formula:

(III)

with a phenol of the formula:

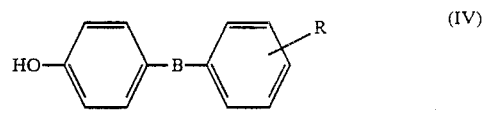
(IV)

in which R and B have the meanings indicated above, to give a compound of the formula:

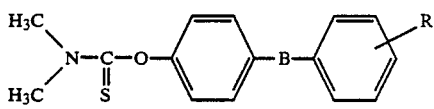

in which R and B have the meanings indicated above, (ii) subject the resulting compound of the formula V to a Newmann rearrangement (J. Org. Chem. (1966) 31, p. 3980), by heating, to give a compound of the formula:

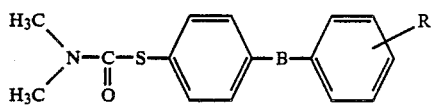

in which R and B have the meanings indicated above, and (iii) treat the resulting compound of the formula VI with a metal alcoholate, preferably sodium or magnesium methanolate, in a $C_1$-$C_4$ lower alcohol, preferably methanol, to give a thiophenol of the formula:

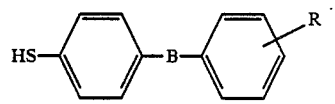

in which R and B have the meanings indicated above.

According to the invention, a therapeutic composition is proposed which contains, in association with a physiologically acceptable excipient, at least one compound selected from the group consisting of the products of the formula I and epimers thereof. Of course, in a composition of this type, the active ingredient is present in a therapeutically effective amount.

The compounds of the formula I are useful in therapy as antithrombotics. They are especially useful in the prevention and treatment of disorders of the venous circulation.

According to the invention, it is recommended to use a substance belonging to the group of compounds of the formula I and epimers thereof in order to prepare an antithrombotic drug to be used in therapy for the treatment of disorders of the venous circulation.

Further characteristics and advantages of the invention will be understood more clearly from the following description of preparative examples, which in no way imply a limitation but are given by way of illustration, and of results of pharmacological tests. The angles of optical rotations $[\alpha]_D^{20}$ are expressed in degrees and were measured at 20° C.

PREPARATION I

Preparation of O-4-(4-nitrobenzoyl)phenyl dimethylthiocarbamate 1.4 g (0.025 mol) of potassium hydroxide pellets are added to a suspension of 5.4 g (0.0224 mol) of 4-hydroxyphenyl 4-nitrophenyl methanone in 60 ml of water. The reaction mixture is heated at 50° C. for two hours, with vigorous stirring. The mixture is then cooled to 0° C. and a solution of 3.5 g (0.029 mol) of dimethylthiocarbamoyl chloride in 15 ml of tetrahydrofuran (THF) is added dropwise. When the addition is complete, the reaction mixture is stirred for 15 minutes at 0° C. and then for one hour at 20° C. The reaction medium is then hydrolyzed in 25 ml of 1N NaOH at 0° C. The precipitate obtained is filtered off and washed with water until the pH of the washings is neutral. After drying, it is recrystallized from a methylene chloride/hexane mixture to give 5.9 g (yield: 84%) of the expected product melting at 168° C.

PREPARATION II

Preparation of S-4-(4-nitrobenzoyl)phenyl dimethylthiocarbamate 5 g of the product obtained in Preparation I are heated at 200°-210° C. for three hours under a nitrogen atmosphere, with stirring. The disappearance of the starting material is monitored by thin layer chromatography using a toluene/ethyl acetate mixture (4:9 v/v) as the eluent. This gives 5 g (quantitative yield) of the expected product melting at 198°-199° C.

PREPARATION III

Preparation of 4-mercaptophenyl 4-nitrophenyl methanone 9.5 g (0.030 mol) of the product obtained in Preparation II are dissolved in 90 ml of dioxane under a nitrogen atmosphere. 0.039 mol of sodium methylate (8% solution in methanol) is added and the disappearance of the starting material is monitored by thin layer chromatography using a hexane/ethyl acetate mixture (1:1 v/v) as the eluent. After stirring for one hour at room temperature, the reaction mixture is hydrolyzed by acidification with a 1N solution of hydrochloric acid at 0° C. The expected product is extracted with ethyl acetate. The organic phase obtained is washed with water until the pH of the washings is neutral, dried over magnesium sulfate and filtered and the solvent is evaporated off to give 7.3 g (yield: 93%) of the expected product melting at 116°-117° C.

PREPARATION IV

Preparation of (4-(4-nitrobenzoyl)phenyl)-2,3,4-tri-O-acetyl-1,5-dithio-β-D-xylopyranoside

EXAMPLE 1a

A mixture of 150 ml of anhydrous benzene, 150 ml of nitromethane and 30 g of a 0.4 nm molecular sieve (marketed by the company E. MERCK) is stirred at room temperature for 15 minutes and 14.2 g (0.0553 mol) of mercuric cyanide (Hg(CN)$_2$) are then added. After the resulting mixture has been stirred for 10 minutes at room temperature, 19.6 g (0.0552 mol) of 2,3,4-tri-O-acetyl-1-bromo-5-thio-α-D-xylopyranoside are added, followed by 13 g (0.050 mol) of 4-mercaptophenyl 4-nitrophenyl methanone in small portions. When the addition is complete, the reaction mixture is heated at 40°-50° C. for four hours and then filtered on Celite ® (i.e. diatomaceous silica for filtration). The residue is washed several times with ethyl acetate. The organic phase obtained is washed successively with a saturated solution of sodium chloride, a 1N solution of NaOH and a solution of sodium chloride and then with water until the pH of the washings is neutral. It is dried over magnesium sulfate and filtered and the solvent is evaporated off. The yellowish oil obtained is dissolved in 50 ml of ether and left at 4° C. for 12 hours. The product crystallizes. After filtration, 17.2 g of the expected product in the β configuration are obtained. The mother liquors are then evaporated and the products which they contain are separated by flash chromatography using a toluene/ethyl acetate mixture (8:1 v/v) as the eluent. This finally gives 18.6 g of the β isomer (yield: 70%) melting at 166°–169° C. ($[\alpha]_D^{20} = +92$; C=0.5 (CHCl$_3$)) and 3.9 g of the α isomer (yield: 15%) in the form of a foam ($[\alpha]_D^{20} = +286$; C=0.5 (CHCl$_3$)).

PREPARATION V

Preparation of (4-(4-nitrobenzoyl)phenyl)-1,5-dithio-β-D-xylopyranoside

EXAMPLE 1

18 g (0.0337 mol) of the product obtained in Preparation IV (Example 1a) are dissolved in a mixture of 100 ml of ethyl acetate and 300 ml of methanol under a nitrogen atmosphere and 8.5 ml of an 8% solution of sodium methylate in methanol are then added. After stirring for two hours at room temperature, the precipitate formed is filtered off and washed twice with 50 ml of methanol. The filtrate obtained is neutralized with Amberlite ® IR 120 resin (H+) to pH 4–5 and then, after filtration, the solvent is evaporated off and the resulting evaporation residue is combined with the precipitate obtained previously. This gives 13.8 g (quantitative yield) of the expected product melting at 183° C. ($[\alpha]_D^{20} = +60$; C=0.5 (DMSO)).

PREPARATION VI

Preparation of (4-((4-nitrophenyl)hydroxymethyl)phenyl)-1,5-dithio-β-D-xylopyranoside

EXAMPLE 3

1.2 g (0.0315 mol) of sodium borohydride are added in small portions, under a nitrogen atmosphere, to a suspension of 11.2 g (0.0275 mol) of the product obtained in Preparation V (Example 1). The solution becomes homogeneous after stirring for two hours at 0° C. The reaction medium is neutralized with Amberlite ® IR 120 resin (H+) to pH 4–5 and the solvent is evaporated off after filtration. The resulting evaporation residue is purified on a silica column using ethyl acetate as the eluent. This gives 11.2 g (quantitative yield) of the expected product melting at 80° C. ($[\alpha]_D^{20} = +8$; C=0.5 (methanol)).

PREPARATION VII

Preparation of (4-((4-nitrophenyl)hydroxymethyl)phenyl)-2,3,4-tri-O-acetyl-1,5-dithio-β-D-xylopyranoside

EXAMPLE 3a 7 g (0.0131 mol) of (4-(4-nitrobenzoyl)phenyl)-2,3,4-tri-O-acetyl-1,5-dithio-β-D-xylopyranoside obtained in Preparation IV (Example 1a) are dissolved in 70 ml of methanol under a nitrogen atmosphere and 0.5 g (0.0131 mol) of sodium borohydride is then added to the reaction mixture at room temperature. The reaction medium is stirred for 30 minutes and then acidified by the addition of Amberlite ® IR 120 resin (H+) to pH 4–5. After filtration, the filtrate which has been collected is evaporated to give 6.3 g (yield: 90%) of the expected product in the form of a yellow foam ($[\alpha]_D^{20} = +29$; C=0.15 (methanol)).

PREPARATION VIII

Preparation of (4-(4-nitrobenzyl)phenyl)-2,3,4-tri-O-acetyl-1,5-dithio-β-D-xylopyranoside 3.3 g (0.00616 mol) of (4-((4-nitrophenyl)hydroxymethyl)phenyl)-2,3,4-tri-O-acetyl-1,5-dithio-β-D-xylopyranoside (Example 3a) obtained in Preparation VII are suspended in 17 ml of methylene chloride under a nitrogen atmosphere. The reaction medium is cooled to 0° C., 17 ml of trifluoroacetic acid are then added all at once and 470 mg (0.0123 mol) of sodium borohydride are added in small portions. The medium is stirred at 0° C. for 1.5 h. The reaction medium is hydrolyzed on ice and extracted with methylene chloride. The organic phase obtained is washed with a saturated solution of bicarbonate and then with water until the pH of the washings is neutral. The organic phase is dried, filtered and then evaporated to give 2.77 g (yield: 87%) of the expected product in the form of a foam.

PREPARATION IX

Preparation of (4-(4-nitrobenzyl)phenyl)-1,5-dithio-β-D-xylopyranoside

EXAMPLE 4

2.79 g (0.00537 mol) of (4-(4-nitrobenzyl)phenyl)-2,3,4-tri-O-acetyl-1,5-dithio-β-D-xylopyranoside obtained in Preparation VIII are suspended in 40 ml of methanol and then 0.15 ml of an 8% solution of sodium methylate in methanol is added at room temperature, with stirring. After stirring for 12 hours at room temperature, the sodium methylate is neutralized with Amberlite ® IR 120 resin (H+). The reaction medium is filtered, the filtrate is evaporated and the resulting evaporation residue is then purified by flash chromatography using a methylene chloride/methanol mixture (95:5 v/v) as the eluent. This gives 1.3 g (yield: 60%) of the expected product melting at 163° C. ($[\alpha]_D^{20} = +10$; C=0.5 (methanol)).

PREPARATION X

Preparation of (4-(4-nitrobenzyl)phenyl)-2,3,4-tri-O-acetyl-5-thio-β-D-xylopyranoside

EXAMPLE 2a 4.5 g (0.01965 mol) of 4-(4-nitrobenzyl)phenol, 3 ml of 2,4,6-trimethylpyridine, 70 ml of a toluene/nitromethane mixture (1:1 v/v) and 10 g of a 0.4 nm molecular sieve are mixed successively at 3° C. under a nitrogen atmosphere. The reaction medium is stirred vigorously for 20 minutes, 5.8 g (0.0225 mol) of silver triflate are then introduced and 8.7 g (0.0245 mol) of 1-bromo-2,3,4-tri-O-acetyl-5-thio-α-D-xylopyranoside are added in 2.17 g portions every 30 minutes. The mixture is stirred at 3° C. for 20 hours in the absence of light. The reaction medium is filtered on Celite ® and the precipitate is washed three times with 200 ml of ethyl acetate. The filtrate obtained is washed with 1N HCl and then with water until the pH of the washings is neutral. After drying over magnesium sulfate, filtration and evaporation, the yellowish oil obtained is purified by flash chromatography using a hexane/ethyl acetate mixture as the eluent. This gives 3 g (yield: 30%) of the β isomer melting at 134° C. ($[\alpha]_D^{20} = -25$; C=0.5 (CHCl$_3$)) and 3 g of the α isomer ($[\alpha]_D^{20} = +284$; C=0.4 (CHCl$_3$)).

PREPARATION XI

Preparation of
(4-(4-nitrobenzyl)phenyl)-5-thio-β-D-xylopyranoside

EXAMPLE 2

2.5 g (0.005 mol) of the product obtained in Preparation X (Example 2a) are suspended in 150 ml of methanol at 0° C. under a nitrogen atmosphere and 0.5 ml of an 8% solution of sodium methylate in methanol is then added. The reaction medium is stirred for two hours and Amberlite® IR 120 resin (H+) is then added. When neutral pH has been reached, the methanol is evaporated off under reduced pressure and the resulting evaporation residue is lyophilized to give 1.9 g (quantitative yield) of the expected product melting at 166° C. ($[\alpha]_D^{20} = -21$; C=0.5 (methanol)).

PREPARATION XII

Preparation of
(4-(4-nitrobenzoyl)phenyl)-2,3,4-tri-O-acetyl-5-thio-β-D-xylopyranoside

EXAMPLE 10a 1.1 g (0.0028 mol) of the product obtained in Preparation X (Example 2a), 50 ml of anhydrous methylene chloride, 0.66 g (0.043 mol) of chromium oxide ($Cr_2O_3$) and 12 ml of pyridine are mixed successively under a nitrogen atmosphere. The resulting mixture is heated at 60° C. for 24 hours, 0.66 g of chromium oxide is then added and heating is continued for 24 hours. The organic phase is separated from the insoluble residue by decantation. The insoluble residue is taken up with a solution of sodium bicarbonate and isopropyl alcohol and then extracted three times with methylene chloride. The organic phases are combined, washed with a solution of sodium bicarbonate, with water until the pH of the washings is neutral, with 1N hydrochloric acid and then with water until the pH of the washings is neutral, dried over magnesium sulfate and filtered and the filtrate is evaporated. The resulting crude evaporation residue is purified by flash chromatography using a chloroform/ethyl acetate mixture (1:1 v/v) as the eluent. This gives 0.720 g of the starting material and 0.260 g (yield: 24%) of the expected product melting at 152° C. ($[\alpha]_D^{20} = -47$; C=0.3 ($CHCl_3$)).

PREPARATION XIII

Preparation of
(4-((4-nitrophenyl)hydroxymethyl)phenyl)-1,5-dithio-β-D-xylopyranoside

EXAMPLE 3

5.33 g (0.01 mol) of the product obtained in Preparation IV (Example 1a) are dissolved in 50 ml of anhydrous methanol under a nitrogen atmosphere and 0.5 ml of an 8% solution of sodium methylate in methanol is then added. The mixture is stirred for 1 hour, the disappearance of the starting material being monitored by thin layer chromatography. When the starting material has totally disappeared, 0.4 mg (0.0105 mol) of sodium borohydride ($NaBH_4$) is added in small portions and the disappearance of the previously formed acetylated intermediate is monitored. Finally, Amberlite® IR 120 resin (H+) is added to the resulting mixture in order to neutralize the medium. After filtration, the filtrate is evaporated to dryness. The evaporation residue, which is obtained in the form of a foam, is taken up with double-distilled water and then lyophilized to give 4 g (quantitative yield) of the expected product melting at 80° C. ($[\alpha]_D^{20} = +8$; C=0.5 (methanol)).

PREPARATION XIV

Preparation of
(4-((4-nitrophenyl)hydroxymethyl)phenyl)-5-thio-β-D-xylopyranoside

EXAMPLE 8

Following the procedure described in Preparation XIII and starting from (4-(4-nitrobenzoyl)phenyl)-2,3,4-tri-O-acetyl-5-thio-β-D-xylopyranoside obtained in Preparation XII, the expected product melting at 108°-118° C. is obtained with a quantitative yield ($[\alpha]_D^{20} = -7$; C=0.5 (methanol)).

PREPARTION XV

Preparation of 4-mercaptophenyl 3-nitrophenyl methanone

Following the procedure described in Preparation I and starting from 18 g (0.07407 mol) of 4-hydroxyphenyl 3-nitrophenyl methanone and 12.3 g (0.0992 mol) of dimethylthiocarbamoyl chloride, 20.5 g (yield: 84%) of O-4-(3-nitrobenzoyl)phenyl dimethylthiocarbamate are obtained.

Following the procedure described in Preparation II and starting from 20.5 g (0.062 mol) of O-4-(3-nitrobenzoyl)phenyl dimethylthiocarbamate, 20.5 g (0.062 mol) (quantitative yield) of S-4-(3-nitrobenzoyl)phenyl dimethylthiocarbamate are obtained.

Following the procedure described in Preparation III and starting from 20.5 g (0.062 mol) of S-4-(3-nitrobenzoyl)phenyl dimethylthiocarbamate, 15.6 g (yield: 96%) of 4-mercaptophenyl 3-nitrophenyl methanone melting at 114° C. are obtained.

PREPARATION XVI

Preparation of 4-cyanophenyl 4-mercaptophenyl methanone

Following the procedure described in Preparation I and starting from 5 g (0.0224 mol) of 4-hydroxyphenyl 3-nitrophenyl methanone and 3.6 g (0.0312 mol) of dimethylthiocarbamoyl chloride, 5.6 g (yield: 76%) of O-4-(4-cyanobenzoyl)phenyl dimethylthiocarbamate melting at 162° C. are obtained.

Following the procedure described in Preparation II and starting from 5.2 g (0.0167 mol) of O-4-(4-cyanobenzoyl)phenyl dimethylthiocarbamate, 5.2 g (quantitative yield) of S-4-(4-cyanobenzoyl)phenyl dimethylthiocarbamate melting at 174° C. are obtained.

Following the procedure described in Preparation III and starting from 18.6 g (0.059 mol) of S-4-(4-cyanobenzoyl)phenyl dimethylthiocarbamate, =12.5 g (yield: 92%) of 4-mercaptophenyl 4-cyanophenyl methanone melting at 156° C. are obtained.

PREPARATION XVII

Preparation of
(4-(4-cyanobenzoyl)phenyl)-2,3,4-tri-O-acetyl-1,5-dithio-β-D-xylopyranoside

EXAMPLE 12a

Following the procedure described in Preparation IV and starting from 6 g (0.0251 mol) of 4-mercaptophenyl 4-cyanophenyl methanone obtained in Preparation XVI, 9.8 g (0.0276 mol) of 2,3,4-tri-O-acetyl-1-bromo-5-thio-α-D-xylopyranoside and 7.1 g (0.0276 mol) of mercuric cyanide, 7.3 g (yield: 52%) of the β isomer melting at 172° C. are obtained ([α]$_D^{20}$=+50; C=0.15 (CHCl$_3$)).

PREPARATION XVIII

Preparation of (4-(4-cyanobenzoyl)phenyl)-1,5-dithio-β-xylopyranoside

EXAMPLE 12

Following the procedure described in Preparation V and starting from 2 g (0.0356 mol) of the product obtained in Preparation XVII (Example 12a) and 0.75 ml of an 8% solution of sodium methylate, 1.38 g (quantitative yield) of the expected product melting at 164° C. are obtained ([α]$_D^{20}$=+53; C=0.197 (CH$_3$OH)).

PREPARATION XIX

Preparation of (4-((4-cyanophenyl)hydroxymethyl)phenyl)-1,5-dithio-β-D-xylopyranoside

EXAMPLE 13

Following the procedure described in Preparation VI and starting from 3.7 g (0.0095 mol) of the product obtained in Preparation XVIII (Example 12) and 0.370 g (0.0097 mol) of sodium borohydride, 3 g (yield: 81%) of the expected product melting at 70°–85° C. are obtained ([α]$_D^{20}$=+2.8; C=0.598 (CH$_3$OH)).

PREPARATION XX

Separation of the two epimers of (4-((4-nitrophenyl)hydroxymethyl)phenyl)-1,5-dithio-β-D-xylopyranoside (1) Preparation of (+)-(4-((4-nitrophenyl)hydroxymethyl)phenyl)-1,5-dithio-β-D-xylopyranoside

EXAMPLE 16

11.2 g of the mixture of epimers ([α]$_D^{20}$=+8; C=0.5 (methanol)) obtained in Preparation VI are recrystallized from 80 ml of ethyl acetate saturated with water. This gives 7.85 g of crystals (C$_1$) ([α]$_D^{20}$=+4; C=0.4 (methanol)) and a filtrate (F$_1$). The crystals (C$_1$) are recrystallized from 150 ml of ethyl acetate containing 1% (v/v) of water. This gives 3.15 g of crystals (C$_2$) ([α]$_D^{20}$=+17.6; C=0.45 (methanol)).

The crystals (C$_2$) are recrystallized from 40 ml of ethyl acetate saturated with water. This gives 1.78 g of crystals (C$_3$) ([α]$_D^{20}$=+23.2; C=0.45 (methanol)).

The crystals (C$_3$) are in turn recrystallized from 16 ml of ethyl acetate saturated with water. This gives 1.43 g of crystals of the (+) isomer melting at 141° C. ([α]$_D^{20}$=+25; C=0.4 (methanol)).

(2) Preparation of (−)-(4-((4-nitrophenyl)hydroxymethyl)phenyl)-1,5-dithio-β-D-xylopyranoside

EXAMPLE 17

The filtrate (F$_1$) is evaporated in vacuo and the residue is taken up with ethyl acetate containing less than 100 ppm of water. After crystallization, 3.9 g of crystals (C'$_2$) are obtained ([α]$_D^{20}$=−4.6; C=0.45 (methanol)).

The crystals (C'$_2$) are recrystallized from 130 ml of ethyl acetate containing less than 100 ppm of water. This gives 1.44 g of crystals (C'$_3$) ([α]$_D^{20}$=−10.4; C=0.35 (methanol)).

The crystals (C'$_3$) are recrystallized from 60 ml of ethyl acetate containing less than 100 ppm of water. This gives 0.96 g of crystals of the (−) isomer melting from 157° to 163° C. ([α]$_D^{20}$=−15; C=0.4 (methanol)).

PREPARATION XXI

Preparation of 2-cyanophenyl 4-mercaptophenyl methanone

Following the procedure described in Preparation I and starting from 13.3 g (0.059 mol) of 2-cyanophenyl 4-hydroxyphenyl methanone and 8.5 g (0.068 mol) of dimethylthiocarbamoyl chloride, 16.5 g (yield: 89%) of O-4-(2-cyanobenzoyl)phenyl dimethylthiocarbamate melting at 138° C. are obtained.

Following the procedure described in Preparation II and starting from 16 g (0.052 mol) of O-4-(2-cyanobenzoyl)phenyl dimethylthiocarbamate, 10.9 g (yield: 68%) of S-4-(2-cyanobenzoyl)phenyl dimethylthiocarbamate melting at 112° C. are obtained.

Following the procedure described in Preparation III and starting from 10.6 g (0.034 mol) of S-4-(2-cyanobenzoyl)phenyl dimethylthiocarbamate, 9 g (yield: 80%) of 2-cyanophenyl 4-mercaptophenyl methanone melting at 102° C. are obtained.

PREPARATION XXII

Preparation of 3-cyanophenyl 4-mercaptophenyl methanone

Following the procedure described in Preparation I and starting from 27 g (0.121 mol) of 3-cyanophenyl 4-hydroxyphenyl methanone and 17.2 g (0.138 mol) of dimethylthiocarbamoyl chloride, 35 g (yield: 88%) of O-4-(3-cyanobenzoyl)phenyl dimethylthiocarbamate melting at 160° C. are obtained.

Following the procedure described in Preparation II and starting from 33 g (0.106 mol) of O-4-(3-cyanobenzoyl)phenyl dimethylthiocarbamate, 25 g (yield: 79%) of S-4-(3-cyanobenzoyl)phenyl dimethylthiocarbamate melting at 150° C. are obtained.

Following the procedure described in Preparation III and starting from 22.6 g (0.073 mol) of S-4-(3-cyanobenzoyl)phenyl dimethylthiocarbamate, 16.5 g (yield: 94.8%) of 3-cyanophenyl 4-mercaptophenyl methanone melting at 126° C. are obtained.

Without implying a limitation, a number of compounds of the formula I according to the invention have been collated in Table I below and a number of their acetylated derivatives have been collated in Table II below.

The physical characteristics of the compounds according to the invention have been summarized in Tables I and II.

The antithrombotic activity of the products according to the invention was demonstrated by the following protocol for venous thrombosis:

A venous stasis is produced under hypercoagulation according to the technique described by WESSLER et al. (J. Applied Physiol. 1959, p. 943–946). As in the technique described by J. HAUPMAN et al. (Thrombosis and Haemostasis 43 (2) 1980, p. 118), the hypercoagulant used is a solution of activated factor X supplied by the company Flow Laboratories (71 Knat per 12.5 ml of physiological serum).

The study is performed on unfasted male Wistar rats weighing 250 to 280 g (groups of 10 animals). The test products are administered orally as a suspension in PEG 400. A thrombosis is induced 4 hours after this treatment and the thrombus formed is removed and weighed. The results obtained at a dose of 12.5 mg/kg p.o. (unless indicated otherwise) have been collated in Table III. The results obtained with the known products of the above-mentioned prior art have also been collated in this Table.

The venous antithrombotic activity of the products according to the invention is 2 to 16 times greater than that of the known products of the prior art.

TABLE I

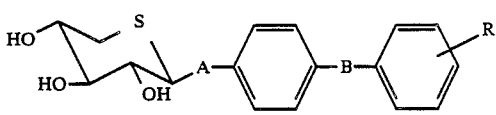

| Ex. | A | B | R | M.p. (°C.) | $[\alpha]_D^{20}$ | (C: % w/v) |
|---|---|---|---|---|---|---|
| 1 | S | CO | 4-NO₂ | 183 | +60 | (0.5) a |
| 2 | O | CH₂ | 4-NO₂ | 166 | −21 | (0.5) b |
| 3 | S | CHOH | 4-NO₂ | 65 to 80 (3)(4) | +8 | (0.5) b |
| 4 | S | CH₂ | 4-NO₂ | 163 (3) | +10 | (0.5) b |
| 5 | S | CHOH | H | 160 to 190 (4) | +11.5 | (0.1) b |
| 6 | S | CHOH | 4-Cl | 169 (3)(4) | +15.5 | (0.1) b |
| 7 | S | CHOH | 3-NO₂ | 60 to 88 (3)(4) | +20.3 | (0.5) b |
| 8 | O | CHOH | 4-NO₂ | 108 to 118 (1)(3)(4) | −7 | (0.7) b |
| 9 | O | CHOH | 4-Cl | 110 to 135 (3)(4) | −26 | (0.18) b |
| 10 | O | CO | 4-NO₂ | 196 | −51 | (0.15) b |
| 11 | O | CO | 4-Cl | 214 | −56 | (0.15) b |
| 12 | S | CO | 4-CN | 164 | +53 | (0.197) b |
| 13 | S | CHOH | 4-CN | 70 to 85 (4) | +2.8 | (0.598) b |
| 14 | O | CH₂ | 4-Cl | 184 | −45 | (0.154) b |
| 15 | S | CO | 4-Cl | 160 (2) | +50 | (0.26) b |
| 16 | S | CHOH | 4-NO₂ | 141 | +25 | (0.4) b |
| 17 | S | CHOH | 4-NO₂ | 157 to 163 | −15 | (0.4) b |
| 18 | S | CO | 3-CN | 210 | +41.2 | (0.5) c |
| 19 | S | CO | 2-CN | 195 | +59.5 | (0.4) b |

Notes:
(1) residual solvent: 2.3% of H₂O
(2) residual solvent: 2.5% of H₂O
(3) lyophilized product
(4) mixture of epimers
a solvent: DMSO
b solvent: CH₃OH
c solvent: THF

TABLE II

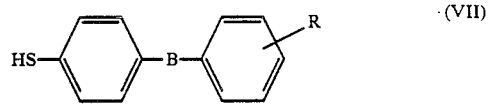

| Ex. | A | B | R | M.p. (°C.) | $[\alpha]_D^{20}$ | (C: % w/v) |
|---|---|---|---|---|---|---|
| 1a | S | CO | 4-NO₂ | 166 to 169 | +92 | (0.5) a |
| 2a | O | CH₂ | 4-NO₂ | 134 | −25 | (0.52) a |
| 3a | S | CHOH | 4-NO₂ | 74 to 98 (1) | +29 | (0.15) b |
| 5a | S | CO | H | 151 | +93 | (0.1) b |
| 7a | S | CO | 3-NO₂ | 142 to 144 | +62 | (0.5) a |
| 10a | O | CO | 4-NO₂ | 152 | −47 | (0.3) a |
| 11a | O | CO | 4-Cl | 146 | −50 | (0.17) a |
| 12a | S | CO | 4-CN | 172 | +50 | (0.15) a |
| 14a | O | CH₂ | 4-Cl | 112 | −40 | (0.5) a |
| 15a | S | CO | 4-Cl | 164 | +105 | (0.1) b |
| 18a | S | CO | 3-CN | 144 | +50.5 | (0.54) a |
| 19a | S | CO | 2-CN | 100 to 110 | +110.4 | (0.5) b |

Notes:
(1) mixture of diastereoisomers
a solvent: CHCl₃
b solvent: CH₃OH

TABLE III

| PRODUCT | % INHIBITION |
|---|---|
| Ex. 1 | 48 |
| Ex. 2 | 76 |
| Ex. 3 | 87 |
| Ex. 3a | 63 |
| Ex. 4 | 72 |
| Ex. 5 | 44 |
| Ex. 6 | 61 |
| Ex. 7 | 68 |
| Ex. 8 | 80 |
| Ex. 9 | 57 |
| Ex. 10 | 65 |
| Ex. 11 | 69 |
| Ex. 12 | 69 |
| Ex. 13 | 83 |
| Ex. 14 | 30 |
| Ex. 15 | 56 |
| Ex. 16 | 72 (1) |
| Ex. 17 | 66 (1) |
| Ex. 18 | 31 |
| Ex. 19 | 54 |
| A | 14 |
| B | 5.5 |

Notes:
A: comparison product described in Example 1 of European Patent Document A-0133103
B: comparison product described in Example 97 of European Patent Document B-0051023
(1): at a dose of 7.5 mg/kg p.o.

What is claimed is:

1. A thiophenol compound selected from the group consisting of compounds that have formula:

(VII)

HS—⟨phenyl⟩—B—⟨phenyl⟩—R wherein
R is a NO₂ or CN group; and
B is a CH₂, CHOH, or CO group.

* * * * *